United States Patent [19]

Auman

[11] Patent Number: 5,260,408
[45] Date of Patent: Nov. 9, 1993

[54] LOW THERMAL EXPANSION COEFFICIENT POLYIMIDES WITH IMPROVED ELONGATION

[75] Inventor: Brian C. Auman, Newark, Del.

[73] Assignee: E. I. du Pont de Nemours and Company, Wilmington, Del.

[21] Appl. No.: 784,353

[22] Filed: Oct. 29, 1991

[51] Int. Cl.⁵ .................. C08G 73/10; C08G 69/26; C08G 63/00
[52] U.S. Cl. .................. 528/183; 528/125; 528/128; 528/172; 528/173; 528/174; 528/176; 528/183; 528/185; 528/188; 528/190; 528/191; 528/220; 528/229; 528/350; 528/353; 428/473.5
[58] Field of Search .......... 528/125, 128, 172–174, 528/176, 183, 185, 188, 190–191, 220, 229, 350, 353; 549/388; 428/473.5

[56] References Cited

U.S. PATENT DOCUMENTS

| | | | |
|---|---|---|---|
| 5,051,520 | 9/1991 | Trofimenko | 528/176 |
| 5,097,000 | 3/1992 | Trofimenko | 528/183 |
| 5,115,090 | 5/1992 | Sachdev et al. | 528/353 |

FOREIGN PATENT DOCUMENTS 2-60933  3/1990  Japan.
3-72528  3/1991  Japan.
WO9101340  2/1991  PCT Int'l Appl..

OTHER PUBLICATIONS

"Polyimides Derived from 2,2'-Bis(trifluoromethyl)-4,-4'-diaminobiphenyl.1. Synthesis and Characterization of Polyimides Prepared with 2,2'-Bis(3,4-dicarboxyphenyl)hexafluoropropane Dianhydride or Pyromellitic Dianhydride," Matsuura, et al, *Macromolecules*, vol. 24, No. 18, 1991, pp. 5001–5005.

*Primary Examiner*—John Kight, III
*Assistant Examiner*—P. Hampton-Hightower

[57] ABSTRACT

Polyimide compositions, films, and electronic devices using polyimides, based on 9,9-bis(perfluoroalkyl)xanthene-2,3,6,7-tetracarboxylic dianhydride or 9-aryl-9(perfluoroalkyl)xanthene-2,3,6,7-tetracarboxylic dianhydride and 3,3',4,4'-biphenyl tetracarboxylic dianhydride or 2,2-bis(3,4-carboxyphenyl)hexafluoropropane dianhydride and benzidine derivatives which offer a combination of desirable properties including, low linear coefficient of thermal expansion, low moisture absorption, high glass transition temperature, low dielectric constant, and improved tensile elongation.

10 Claims, No Drawings

LOW THERMAL EXPANSION COEFFICIENT POLYIMIDES WITH IMPROVED ELONGATION

FIELD OF THE INVENTION

This invention relates to polyimide compositions, films, and electronic devices using polyimides, based on 9,9-bis(perfluoroalkyl)xanthene-2,3,6,7-tetracarboxylic dianhydride or 9-aryl-9-(perfluoroalkyl)xanthene-2,3,6,7-tetracarboxylic dianhydride, and benzidine derivatives, which have been modified with 3,3',4,4'-biphenyl tetracarboxylic dianhydride or 2,2-bis(3,4-carboxyphenyl)hexafluoropropane dianhydride in order to provide low linear coefficient of thermal expansion and improved tensile elongation.

BACKGROUND OF THE INVENTION

Polyimides constitute a class of valuable polymers being characterized by thermal stability, inert character, usual insolubility in even strong solvents, good mechanical and electrical properties and high Tg, among others. Their precursors are usually polyamic acids, which may take the final imidized form either by thermal or by chemical treatment.

Polyimides have always found a large number of applications requiring at least some of the aforementioned characteristics in numerous industries, and recently their applications have started increasing dramatically in electronic devices, especially as dielectrics. With continuously escalating sophistication in such devices, the demands on the properties and the property control are becoming rather vexatious.

Especially for the electronics industry, improvements of polyimides are needed in forming tough, pin-hole free coatings, having low dielectric constant, low moisture absorption, low linear coefficient of thermal expansion, and good mechanical properties among others. It is not usually possible to maximize all properties, since many of them are antagonistic. Thus, only a compromised solution is usually achieved by at least partially sacrificing one or more of these properties in order to maximize a desired one.

An especially important property for electronics, and other applications as well, is low linear thermal expansion coefficient. This is because in electronic components, differences in the expansion coefficients of the components that make up the electronic device can generate stresses in the device which may lead to premature device failure. As electronic components become ever smaller, control of stress becomes an ever greater concern, such that the thermal expansions of the various components of a device should be matched as closely as possible. Since the stress can generally be related to the product of the difference in thermal expansion of the components and the moduli of those components, control of these factors is important in minimizing stress. Polymers generally have much higher thermal expansion coefficients than other components which make up electronics devices, e.g. silicon, silicon dioxide, copper, aluminum, etc., so that often the large mismatch between polymer and the other components of the device can lead to high stresses within the device. Attempts to reduce the stresses between polymers and the other materials have generally focused on reducing the thermal expansion coefficient mismatch between materials, although it is also possible to reduce stress by reducing modulus.

In polyimides, low thermal expansion coefficient has generally been achieved by the use of a stiff, rod like backbone. An example of this is the polyimide based on 3,3',4,4'-biphenyltetracarboxylic dianhydride (BPDA) and p-phenylene diamine (PPD). This polyimide, depending on processing conditions, can have a linear thermal expansion coefficient in the plane of the film in the range of 3–4 ppm which closely approximates that of silicon such that the stress between silicon and polyimide can be very low. Although this polymer has a low thermal expansion coefficient as well as other desirable properties, it does not have low dielectric constant. My U.S. patent application Ser. No. 07/720,680, filed on Jun. 25, 1991, abandoned describes fluorinated, low thermal expansion coefficient polyimides based on 9-aryl-9-(perfluoroalkyl)-xanthene-2,3,6,7-tetracarboxylic dianhydride or 9,9-bis(perfluoroalkyl)-xanthene-2,3,6,7-tetracarboxylic dianhydride and benzidine derivatives which exhibit a unique combination of low thermal expansion coefficient, low moisture absorption and low dielectric constant. These polyimides, however, because of their very stiff, rigid backbone have relatively low elongation. It is therefore very desirable to provide polyimides which substantially maintain the desirable properties of low dielectric constant and low thermal expansion coefficient while providing improved tensile elongation (higher than 10%).

U.S. Pat. No 5,051,520, (Trofimenko) discloses monomers and polyimides in general based on 9-aryl-9-(perfluoroalkyl)-xanthene-2,3,6,7-tetracarboxylic dianhydride and 9,9-bis(perfluoroalkyl)-xanthene-2,3,6,7-tetracarboxylic dianhydride Japanese Patent Application Publication Kokai Hei 2-60933 (Masaki Ishisawa et al., Pub. Date: Mar. 1, 1990) discloses certain compositions of polyimides containing benzidine derivative and derivatives containing fluorochains.

Japanese Patent Application Publication Kokai Hei 3-72528 (Tetsu Matsuura et al., Pub. Date Mar. 27, 1991) discloses certain compositions of polyimides containing benzidine derivatives and as well as 3,3',4,4'-biphenyltetracarboxylic dianhydride or 2,2-bis(3,4-carboxyphenyl)hexafluoropropane.

International Publication No. WO 91/01340 (Harris, Pub. Date Feb. 7, 1991) discloses benzidine derivatives with miscellaneous dianhydrides.

None of the above references describes, suggests or implies the combination of materials and critical requirements of the present invention; namely a polyimide comprising the structure:

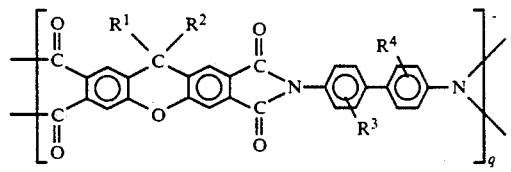

wherein
$R^1$ is aryl or $R^2$,
$R^2$ is $-CF_3$,
$R^3$ and $R^4$ are selected from the group consisting of
$-C_mF_{2m+1}$, $-C_pH_{2p+1}$, and $-OC_pH_{2p+1}$
m is an integer 0–4,
p is an integer 0–2, and
q is an integer greater than 10, the polyimide also comprising an effective molar amount of

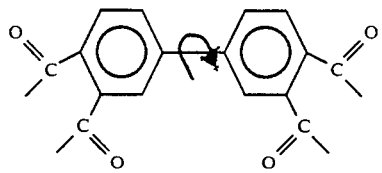

or

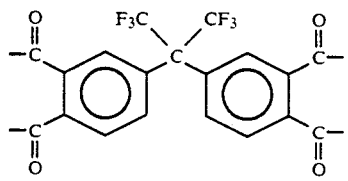

or a combination thereof replacing in the polyimide structure an equivalent molar amount of

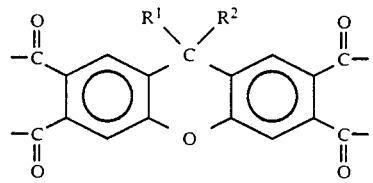

to render the tensile elongation of the polyimide higher than 10%, without raising the value of the linear coefficient of thermal expansion of the polyimide to higher than 25, and the value of the dielectric constant to higher than 3.

SUMMARY OF THE INVENTION

The present invention provides polyimides based on 9-aryl-9-(perfluoroalkyl)-xanthene-2,3,6,7-tetracarboxylic dianhydride or 9,9-bis(perfluoroalkyl)xanthene-2,3,6,7-tetracarboxylic dianhydride and benzidine derivatives, which are modified with an effective amount of 3,3',4,4'-biphenyltetracarboxylic dianhydride or 2,2-bis(3,4-carboxyphenyl)hexafluoropropane to give a good balance of low thermal expansion coefficient, low dielectric constant, and improved tensile elongation. More particularly it pertains to a polyimide comprising the structure:

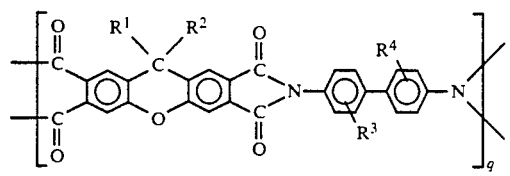

wherein
$R^1$ is aryl or $R^2$,
$R^2$ is —$CF_3$,
$R^3$ and $R^4$ are selected from the group consisting of —$C_mF_{2m+1}$, —$C_pH_{2p+1}$, and —$OC_pH_{2p+1}$
m is an integer 0–4,
p is an integer 0–2, and
q is an integer greater than 10, the polyimide also comprising an effective molar amount of

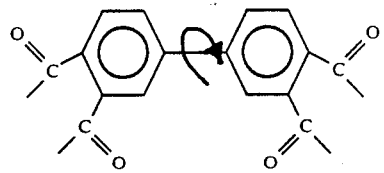

or

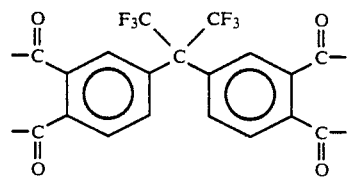

or a combination thereof replacing in the polyimide structure an equivalent molar amount of

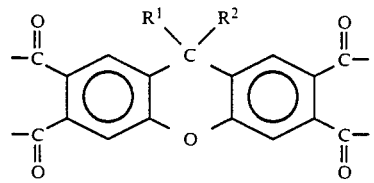

to render the tensile elongation of the polyimide higher than 10%, without raising the value of the linear coefficient of thermal expansion of the polyimide to higher than 25, and the value of the dielectric constant to higher than 3.

Preferably, in the above polyimide
$R^3$ and $R^4$ are in 2, 2'-positions, respectively, in the benzidine ring, and are selected from the group consisting of —$C_mF_{2m+1}$ and —$C_pH_{2p+1}$,
m is an integer 1–4, and
p is an integer 1–2.

The 2, 2'- positions on the benzidine ring are preferred, because electron withdrawing groups, such as for example perfluorinated groups, reduce the reactivity of the amine groups (being in positions 4, 4') of the benzidine derivative if they are in the 3, 3' positions. They may also reduce the reactivity of the benzidine amino groups, due to steric effects in a similar manner as non-electron-withdrawing groups, such as for example hydrocarbon chains, may do.

$R^3$ and $R^4$ may each take the form of a single chlorine atom in the benzidine ring, which however, is in most cases undesirable for electronic applications, due to potential for corrosion.

Also, preferably, both $R^1$ and $R^2$ are —$CF_3$.

Also it is preferable that $R^3$ and $R^4$ are —$CF_3$, and even more preferable that all $R^1$, $R^2$, $R^3$, and $R^4$ are —$CF_3$.

The instant invention also pertains to films comprising polyimides as defined above.

In addition, this invention is also directed to electronic devices containing a conductor or semiconductor comprising:

(a) a substrate which comprises a conductor, semiconductor, or insulator; and (b) a dielectric film in contact with the substrate, the dielectric film comprising a polyimide derived from a fluoroxanthene derivative, a benzidine ring derivative, and an effective amount of 3,3',4,4'-biphenyltetracarboxylic dianhydride or 2,2-bis(3,4-carboxyphenyl)hexafluoropropane as defined above.

By the expression "in contact with the substrate" it is meant that the film is required to be in contact with the conductor, or the semiconductor, or the insulator, or any combination thereof.

DETAILED DESCRIPTION OF THE INVENTION

This invention is directed to polyimide compositions, films, and electronic devices using polyimides based on 9-aryl-9-(perfluoroalkyl)-xanthene-2,3,6,7-tetracarboxylic dianhydride or 9,9-bis(perfluoroalkyl)-xanthene-2,3,6,7-tetracarboxylic dianhydride and benzidine derivatives, which are modified with effective amounts of 3,3',4,4'-biphenyltetracarboxylic dianhydride or 2,2-bis(3,4-carboxyphenyl)hexafluoropropane to give a good balance of low thermal expansion coefficient, low dielectric constant, and improved tensile elongation (higher than 10%).

As aforementioned, polyimides are needed in order to form tough, pin-hole free coatings, having one or more desirable properties, such as low dielectric constant, low linear coefficient of thermal expansion, low moisture absorption, high thermal stability, high glass transition temperature, and high modulus, good tensile elongation, among others. It is not usually possible to maximize all properties since many of them are antagonistic, but it is highly desirable to obtain the best possible balance of these in order to provide a best fit with the requirements of the industry.

In my application Ser. No. 07/720,680, filed on Jun. 25, 1991, abandoned there were disclosed polyimide compositions based on 9-aryl-9-(perfluoroalkyl)-xanthene-2,3,6,7-tetracarboxylic dianhydride or 9,9-bis-(perfluoroalkyl)xanthene-2,3,6,7-tetracarboxylic dianhydride and benzidine derivatives. These fluorinated polyimides were found to give an excellent combination of low dielectric constant, low moisture absorption, and low thermal expansion coefficient. Compared to some conventional materials, however, these polyimides were found to have low tensile elongation. Tensile elongation is in a general way related to toughness, so that films and other articles with low elongation may be susceptible to cracking and other brittleness phenomena during processing, handling, or use. It is desirable, therefore, that the elongation of a polyimide be maximized, while substantially maintaining the other desirable properties of the polyimide, especially low dielectric constant, low moisture absorption, and low thermal expansion coefficient. From these properties, low linear coefficient of thermal expansion and low dielectric constant are of particular importance for many applications involving electronic devices.

The linear coefficient of thermal expansion is considered to be low if it has a value of 25 ppm, or lower. This is because the components involved, such as for example conductors, semiconductors, and inorganic dielectrics or insulators have linear coefficients of thermal expansion (CTE) in the range of 0-25 ppm. For example, the CTE of silicon dioxide is 0.4 ppm, the CTE of silicon is 3-4 ppm, the CTE of aluminum oxide is 6 ppm, the CTE of copper is 17 ppm, and the CTE's of gold, aluminum and silver are in the range of 10-25 ppm. Although it is preferable to have a perfect match of the CTE's of the substrate and the polyimide coating, this is impractical in most cases, since a variety of materials are involved within the same electronic device, such as for example circuitry on even a single silicon wafer. Depending on the particular case, CTE's closer to a narrower sub-range within the broader 0-25 ppm range may be desired. In general CTE's in the range 0-10 ppm are preferable, and CTE's in the range 0-5 ppm are even more preferable as they are close to the CTE's of silicon dioxide and silicon, both being the most common materials found in the semiconductor devices.

It should also be noted that, to some extent, the linear thermal expansion coefficient that is obtained for a polyimide film depends on processing conditions, such as for example, solution concentration, spin coating speed, viscosity, drying and curing profile, and film thickness. This can cause the CTE of a particular polyimide structure to vary over a range; but in general, the rigidity of the polymer chain will determine in what range the CTE will fall.

The dielectric constant is considered to be low if it is lower than 3.0 under dry conditions, and preferably lower than 2.8 and most preferably lower than 2.5. A dielectric constant of over 3.0 is less desirable, or it may even become unacceptable for a number of applications, especially as electronic circuitry becomes smaller and circuit patterns become finer.

The moisture absorption in the case of polyimides at 85% RH is considered to be low when it is less than 2.5%, preferably less than 2.0% and even more preferably less than 1 5%. As a matter of fact, the lower the moisture absorption, the more preferred the polyimide is, provided there is no degradation of the rest of the important properties.

The tensile elongation of polyimide films is considered to be good, if it has a value of at least 10% or more, preferably 20% or more, and even more preferably a value of 25% or more.

In order to increase the elongation of the very stiff, rigid, substantially rod-like, structure of polyimides based on 9-aryl-9-(perfluoroalkyl)-xanthene-2,3,6,7-tetracarboxylic dianhydride or 9,9-bis(perfluoroalkyl)xanthene-2,3,6,7-tetracarboxylic dianhydride and benzidine derivatives, it was found by the inventor that comonomers like 3,3',4,4'-biphenyl tetracarboxylic dianhydride and 2,2-bis(3,4-carboxyphenyl)hexafluoropropane dianhydride may provide enough flexibility to the polymer and thus improve elongation without seriously detracting from the other desirable properties such as low dielectric constant, low moisture absorption, and low thermal expansion coefficient. The first of these comonomers, 3,3',4,4'-biphenyl tetracarboxylic dianhydride (BPDA) is especially interesting because it can impart higher elongation while maintaining very low CTE. The polyimide based on BPDA/PPD, typically yields very low CTE while having a good tensile elongation (typically 20% or higher). It does not, however, have low dielectric constant in contrast to the copolyimides of the present invention.

One may speculate that the useful properties of BPDA result from its fairly unusual structure. Simplified, BPDA can be thought of as existing in the polyimide in two general conformations A and B:

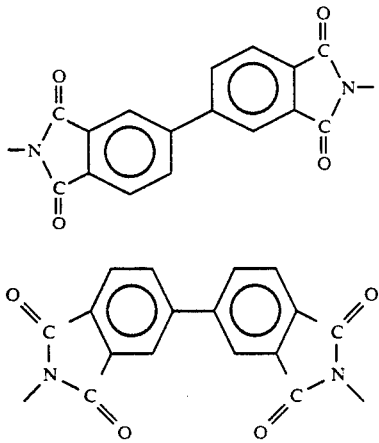

A

B or in general

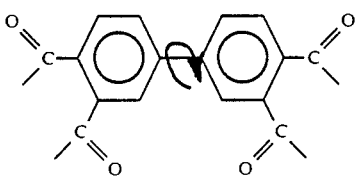

In conformation A, the bonds which link the unit to the other monomer are not colinear, but are antiparallel, such that they maintain a 180° angle to one another but are offset from one another. Such a monomer or conformation is often termed "offset" or "crankshaft" in the art and would be expected to substantially maintain a rod-like nature of the polymer chain when paired with other rod-like monomers, thus yielding high in-plane orientation of the polymer chain and therefore low CTE. In conformation B, the linking bonds are neither colinear or antiparallel, and in fact form about a 120° angle. Such a conformation would not be expected to give a rod-like structure and therefore would give lower orientation and therefore higher CTE; it would, however, increase the chain flexibility and therefore potentially provide higher elongation. Whether the crankshaft (offset) structure or a finite amount of conformation B in the overall structure, or some other aspect of chain dynamics provides the improved elongation is not yet fully understood, but it is believed that because of the low thermal expansion coefficient observed in the examples of the present invention that the BPDA units in the polyimide probably exist in substantially the A conformation. Of course, there would be expected to be other intermediate conformations between A and B because of the rotation about the central biphenyl C—C bond, but these conformations would be expected to give behavior intermediate to those of A and B. These comments, however, are mere speculations and they should not be consrtued to restrict the scope of this invention. In any case, the use of BPDA as a comonomer in the copolyimides of the present invention is especially preferred when it is desired to maintain a very low CTE while providing higher elongation.

A second useful monomer for improving the elongation of polyimides based on 9-aryl-9-(perfluoroalkyl)-xanthene-2,3,6,7-tetracarboxylic dianhydride or 9,9-bis(perfluoroalkyl)-2,3,6,7-xanthene tetracarboxylic dianhydride and rod-like diamines as aforementioned is 2,2-bis(3,4-carboxyphenyl)-hexafluoropropane dianhydride (6FDA). This monomer is different from BPDA in that it has largely bent conformations, and thus would only be used in relatively small amounts if a very low CTE is desired. On the other hand, for certain applications a controllably higher CTE may be desired. If for example, it is desired to substantially match the CTE of a substrate other than silicon, say copper, the CTE of which is 17, it is preferable to use 6FDA as a comonomer, not only to improve the elongation but also to increase the CTE of the polyimide to match that of copper. This is detailed in Example 4. This may also be especially advantageous as the modulus of the copolyimide may be reduced, thus further minimizing stress.

The relative differences between BPDA and 6FDA as comonomers in the copolyimides of the present invention are illustrated by comparing Example 3 to Example 4. In these examples, the elongations achieved using 6FDA are similar or higher than those obtained with BPDA. On the other hand, the CTEs using BPDA are significantly lower than for 6FDA.

It is also contemplated that other "flexibilizing" monomers similar to 6FDA may also prove useful in improving elongation of the very stiff, rod-like polyimides. Such monomers include but are not limited to: oxydiphthalic anhydride, 3,3',4,4'-benzophenone tetracarboxylic dianhydride, 3,3',4,4'-diphenylsulfone tetracarboxylic dianhydride, and the like. In addition to dianhydrides, "flexibilizing" diamines may also prove useful in the practice of the present invention, Such diamines include but are not limited to: 4,4-diaminodiphenylether (4,4'-oxydianiline), m-phenylene diamine, 2,2-bis(4-aminophenyl)hexafluoropropane, 4,4'-methylenedianiline, 3,4'-diaminodiphenylether, 1,4-bis(4-aminophenoxy)benzene, and the like. 6FDA, however, was considered a preferable comonomer in the present invention because of its known ability to reduce moisture absorption and dielectric constant in polyimides.

It is also contemplated that other monomers similar in their crankshaft nature to BPDA may also prove useful in the practice of the present invention. Examples of such monomers, however, are fairly rare and thus BPDA was considered as a preferable monomer for the practice of the present invention.

Other rod-like diamines, such as 1,4-phenylenediamine, or p-phenylenediamine, for example, may be used to replace partially or totally the benzidine derivative in the structure of the polyimide of the present invention. However, the benzidine derivatives as claimed are preferable.

Small amounts of other dianhydrides, such as for example pyromellitic dianhydride, may be used as modifiers.

Electronic devices, such as for example silicon wafers which may contain electronic components, such as conductors, semiconductors, insulators, and combinations thereof, may be coated with the compositions of the present invention. Other examples include printed circuits, hybrid circuits, and the like. The compositions of the present invention in the form of dielectric or protective films are characterized by low linear coefficient of thermal expansion, low dielectric constant, high glass transition temperature, high thermal stability and improved elongation as illustrated in Examples 3 and 4. In some cases, low moisture absorption is also achieved.

Thus, a dielectric film made from an exemplary composition of the present invention, based on 9,9-bis(trifluoromethyl)xanthene-2,3,6,7-tetracarboxylic dianhydride, 3,3'4,4'-biphenyl tetracarboxylic dianhydride, and 2,2'-bis(trifluoromethyl)-benzidine (Example 3) was found to have a linear in-plane coefficient of thermal expansion (CTE) of 7 ppm, moisture absorption of 1.3% at 85% RH, a dry dielectric constant of about 2.7, and a tensile elongation of about 22%. Similar properties were obtained from a similar composition but without 3,3'4,4'-biphenyl tetracarboxylic dianhydride (Comparative Example I), however, the elongation was only 6%.

Another dielectric film made from a different exemplary composition of the present invention based on 9,9-bis(trifluoromethyl)xanthene-2,3,6,7-tetracarboxylic dianhydride, 2,2-bis(3,4-dicarboxyphenyl)hexafluoropropane dianhydride, and 2,2'-bis(trifluoromethyl)benzidine (Example 4). Compared to Comparative Example I, this material had a CTE of 18 ppm, but, it exhibited an elongation of 29%.

Examples of preferred solvents, which may be used in the practice of the present invention are polar organic solvents, such as sulfoxide type solvents including dimethylsulfoxide, diethylsulfoxide, and the like, formamide type solvents including N,N-dimethylformamide, N,N-diethylformamide, and the like, acetamide type solvents including N,N-dimethylacetamide, N,N-diethylacetamide, and the like, pyrrolidone type solvents including N-methyl-2-pyrrolidone, N-cyclohexyl-2-pyrrolidone, 1,3-dimethyl-2-imidozolidione, N-vinyl-2-pyrrolidone, and the like, phenolic solvents including phenol, o-, m-, p-cresol, xylenol, halogenated phenol, catechol, and the like, hexamethylphosphoramide, and a number of lactones including γ-butyrolactones. These solvents may be used alone or as a mixture. Partial use of aromatic hydrocarbons such as xylene, toluene, and the like, is also possible, and sometimes desirable, when for example removal of water as an azeotrope is needed.

GLOSSARY

BPDA: 3,3',4,4'-biphenyltetracarboxylic dianhydride
CTE: Linear Coefficient of Thermal Expansion
DMAC: Dimethylacetamide
DMSO: Dimethylsulfoxide
DSC: Differential Scanning Calorimetry
GPa: Gigapascal
GPC: Gel Permeation Chromatography
mmole: Millimole
Mn: Number average molecular weight
MPa: Megapascal
Mw: Weight average molecular weight
NMP: N-methyl-2-pyrrolidone
ppm: Parts per million
R.H. Relative Humidity
Tg: Glass transition temperature
TGA: Thermogravimetric analysis
THF: Tetrahydrofuran
TMA: Thermomechanical analysis All parts and percentages are given by weight unless otherwise stated.

EXAMPLE 1

Synthesis of Copoly(amic Acid) Based on 9,9-Bis(trifluoromethyl)xanthene-2,3,6,7-tetracarboxylic Dianhydride, 3,3',4,4'-Biphenyl Tetracarboxylic Dianhydride and 2,2'-Bis(trifluoromethyl)benzidine Into a 100 ml reaction kettle fitted with a nitrogen inlet and outlet and a mechanical stirrer were charged 3.7281 g (8.136 mmol) of 9,9-bis(trifluoromethyl)xanthene-2,3,6,7-tetracarboxylic dianhydride, 0.7979 g (2.712 mmol) 3,3',4,4'-biphenyl tetracarboxylic dianhydride and 3.4740 g (10.848 mmol) of 2,2'-bis(trifluoromethyl)benzidine. Shortly thereafter, 42 ml of NMP and were added and stirring was begun. The dianhydrides dissolved slowly into the reaction mixture and the temperature was maintained at room temperature overnight (ca. 20 hrs) under nitrogen. Afterwards, the polymer solution was slowly pressure filtered through a 1 micron filter to yield a clear yellow solution. GPC (DMAc/LiBr/H3P04/THF solvent, polystyrene standards, RI detection) of the poly(amic acid) revealed an Mn=107000 and an Mw=226000, Mw/Mn=2.11.

EXAMPLE 2

Coating of Silicon Wafer with the Poly(amic Acid) of Example 1 and Conversion to Polyimide Part of the clear solution of Example 1 was spin coated onto 5" silicon wafers containing a thin (1000 Å) oxide layer. After spin coating, the wafers were immediately placed in an air oven at 135° C. for 30 min., then placed into another oven under nitrogen and heated at 2° C./min to 200° C. and held for 30 min and then heated at 2° C./min to 350° C. and held for 1 hr. under nitrogen. The resulting polyimide films were coherent and adhered to the wafer.

EXAMPLE 3

Evaluation of the Dielectric Film of Example 2

In order to determine the properties of the dielectric film made in Example 2, the oxide layer of the silicon wafer was etched in aqueous HF. It yielded a free standing polyimide film which was pale yellow in color and creasable. The thickness of the film was 10.0 micrometers and gave the following mechanical properties when tested on an Instron Model 4501 per ASTM D 882-83 (Method A): Tensile Strength=285 MPa, Young's Modulus=5.2 GPa, Tensile Elongation at Break=22%. The linear coefficient of thermal expansion (CTE) from 0°-200° C. when measured by TMA at 5° C./min was found to be 7 ppm by two separate measurements. TGA (15° C./min, 50°-600° C., in air) revealed the onset of appreciable weight loss to be about 435° C. under these conditions. The dielectric constant of the dried film at 0% R.H. and 1 MHz was found to be 2.7, 2.6 and 2.9 by three separate measurements. The moisture absorption of a ~3 micron film spin coated onto a quartz crystal and measured on a quartz crystal microbalance was 1.3% at 85% RH. The glass transition temperature (Tg) as measured as the peak maximum in the loss modulus (E") by dynamic-mechanical analysis (DMA) at a frequency of 10 rad/s was found to be 390° C.

EXAMPLE 4

Synthesis, Use and Evaluation of the Copolyimide Based on 9,9-Bis(trifluoromethyl)xanthene-2,3,6,7-tetracarboxylic Dianhydride, 2,2-Bis(3,4-carboxyphenyl)hexafluoropropane Dianhydride and 2,2'-Bis(trifluoromethyl)benzidine Similar to the procedure of Example 1, a poly(amic acid) was prepared from 3.5638 g (7.7773 mmol) 9,9-bis(trifluoromethyl)xanthene-2,3,6,7-tetracarboxylic dianhydride, 1.1517 g (2.5925 mmol) 2,2-bis(3,4-carboxyphenyl)hexafluoropropane dianhydride and 3.3208 g (10.3697 mmol) of 2,2'-bis(trifluoromethyl)benzidine in 32 ml NMP. The 9,9-bis(trifluoromethyl)xanthene-2,3,6,7-tetracarboxylic dianhydride was added as a solid to the solution of the other two monomers in NMP. After overnight reaction, the viscosity of the reaction mixture had increased substantially, so an additional 10 ml of NMP was added and the reaction was allowed to proceed for an additional 3 days. GPC (DMAc/LiBr/H3PO4/THF solvent, polystyrene standards, RI detection) of the poly(amic acid) revealed an Mn=63500 and an Mw=147000, Mw/Mn=2.32. The polymer was filtered as in Example 1, coated and converted to the polyimide as in Example 2. As in Example 3, a free standing film was obtained which gave the following mechanical properties: Tensile Strength=228 MPa, Young's Modulus=4.3 GPa, Tensile Elongation at Break=29%. The linear coefficient of thermal expansion (CTE) from 0°-200° C. when measured by TMA at 5° C./min was found to be 18 ppm. TGA (15° C./min, 50°-600° C., in air) revealed the onset of appreciable weight loss to be about 446° C. under these conditions.

COMPARATIVE EXAMPLE

EXAMPLE I

Synthesis, Use and Evaluation of the Polyimide Based on 9,9-Bis(trifluoromethyl)xanthene-2,3,6,7-tetracarboxylic Dianhydride and 2,2'-Bis(trifluoromethyl)benzidine Similar to the procedure of Example 1, a poly(amic acid) was prepared from 4.7090 g (10.2766 mmol) of 9,9-Bis(trifluoromethyl)xanthene-2,3,6,7-tetracarboxylic dianhydride and 3.2910 g (10.2766 mmol) of 2,2'-bis(trifluoromethyl)benzidine. Shortly thereafter, 42 ml of NMP were added and stirring was begun. The dianhydride dissolved slowly into the reaction mixture and the temperature was maintained at room temperature overnight (ca. 20 hrs.). GPC (DMAc/LiBr/H3P04/THF solvent, polystyrene standards, RI detection) of the poly(amic acid) solution revealed an Mn=126000 and an Mw=215000, Mw/Mn=1.71. The polymer was filtered as in Example 1, coated and converted to the polyimide as in Example 2. As in Example 3, a free standing film of 10.3 micron thickness gave the following mechanical properties: Tensile Strength=200 MPa, Young's Modulus=6.1 GPa and Tensile Elongation at Break=6%. The coefficient of thermal expansion (CTE) of the film measured by TMA (10° C./min, 0°-200° C.) was found to be 5 ppm and 7 ppm by two separate measurements. The dielectric constant on the dried film at 1 MHz was 2.4 and 2.7 by two separate measurements. The moisture absorption of a -3 micron film spin coated onto a quartz crystal and measured on a quartz crystal microbalance was 1.2% and 1.4% at 85% RH by two separate measurements. The Tg as measured as in Example 3 was found to be ~420° C.

What is claimed is:

1. A polyimide comprising the structure:

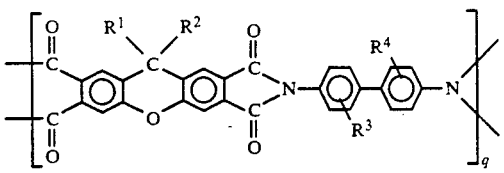

wherein
R$^1$ is aryl or R$^2$,
R$^2$ is —CF$_3$,
R$^3$ and R$^4$ are —C$_m$F$_{2m+1}$, and are in the 2,2'-positions respectively in the benzidine ring,
m is an integer 1-4, and
q is an integer greater than 10,
the polyimide also comprising an effective molar amount of

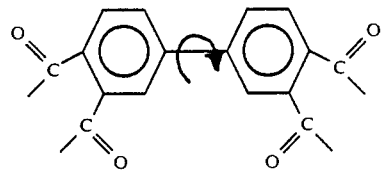

or

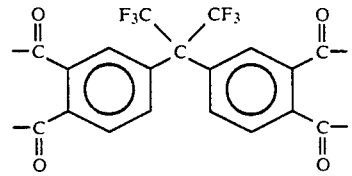

or a combination thereof replacing in the polyimide structure an equivalent molar amount of

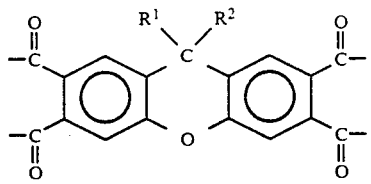

to render the tensile elongation of the polyimide higher than 10%, without raising the value of the linear coefficient of thermal expansion of the polyimide to higher than 25, and the value of the dielectric constant to higher than 3.

2. A polyimide as defined in claim 1, wherein R$^1$ is phenyl.

3. A polyimide as defined in claim 1, wherein R$^1$ and R$^2$ are —CF$_3$.

4. A polyimide as defined in claim 1, wherein R$^3$ and R$^4$ are —CF$_3$.

5. A polyimide as defined in claim 1, wherein R$^1$, R$^2$, R$^3$, and R$^4$ are —CF$_3$.

6. A film comprising a polyimide comprising the structure:

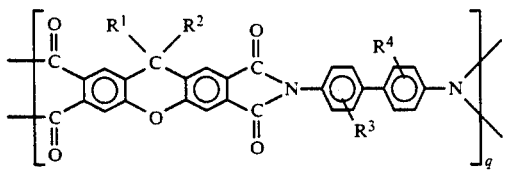

wherein
- $R^1$ is aryl or $R^2$,
- $R^2$ is $-CF_3$,
- $R^3$ and $R^4$ are $-C_mF_{2m+1}$, and are in the 2,2'-positions respectively in the benzidine ring,
- m is an integer 1-4, and
- q is an integer greater than 10, the polyimide also comprising an effective molar amount of

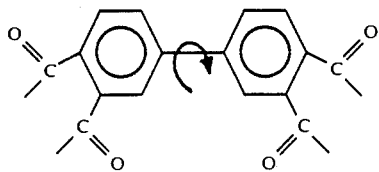

or

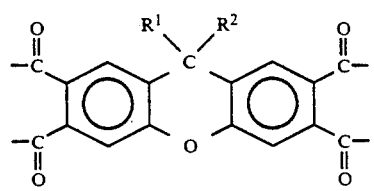

or a combination thereof replacing in the polyimide structure an equivalent molar amount of to render the tensile elongation of the polyimide higher than 10%, without raising the value of the linear coefficient of thermal expansion of the polyimide to higher than 25, and the value of the dielectric constant to higher than 3.

7. A film as defined in claim 6, wherein $R^1$ is phenyl.

8. A film as defined in claim 6, wherein $R^1$ and $R^2$ are $-CF_3$.

9. A film as defined in claim 6, wherein $R^3$ and $R^4$ and $-CF_3$.

10. A film as defined in claim 6, wherein $R^1$, $R^2$, $R^3$, and $R^4$ are $-CF_3$.

* * * * *